United States Patent
Saud et al.

(10) Patent No.: US 6,489,492 B2
(45) Date of Patent: Dec. 3, 2002

(54) CHIRAL DERIVATIVES OF GARCINIA ACID BEARING LACTONE RING MOIETY AND PROCESS FOR PREPARING THE SAME

(75) Inventors: Ibrahim Ibnu Saud, Quilon (IN); Grace Thomas, Pala (IN); Paleappadam Vavan Sasi, Kottayam (IN)

(73) Assignee: Department of Science and Technology, New Delhi (IN)

( * ) Notice: Subject to any disclaimer, the term of this patent is extended or adjusted under 35 U.S.C. 154(b) by 0 days.

(21) Appl. No.: 09/947,198

(22) Filed: Sep. 5, 2001

(65) Prior Publication Data

US 2002/0137950 A1 Sep. 26, 2002

(30) Foreign Application Priority Data

Oct. 3, 2000 (IN) ...................................... 885/DEL/2000

(51) Int. Cl.$^7$ ....................... C07D 307/56; C07D 497/02
(52) U.S. Cl. ........................................ 549/318; 548/453
(58) Field of Search .......................... 548/453; 549/318, 549/322

(56) References Cited

U.S. PATENT DOCUMENTS

| | | | |
|---|---|---|---|
| 3,764,692 A | * 10/1973 | Lowenstein | 424/279 |
| 4,005,086 A | 1/1977 | Guthrie et al. | 260/247 |
| 4,006,166 A | 2/1977 | Guthrie et al. | 260/343.6 |
| 4,007,208 A | 2/1977 | Guthrie et al. | 260/343.6 |
| 5,536,516 A | 7/1996 | Moffet et al. | 426/271 |
| 6,147,228 A | 11/2000 | Ibnusaud et al. | 549/318 |

FOREIGN PATENT DOCUMENTS

| WO | WO 9605741 | 2/1996 |
|---|---|---|
| WO | WO 9636585 | 11/1996 |

OTHER PUBLICATIONS

Lowenstein, John M. 'Garcinia acid or its derivatives for preventing fatty acid deposits in a biological system' CA 75:67483 (1971).*
Chemical Abstracts, vol. 86, 1977, p. 340, Section 86:186629r.
3–Biochem. Interactions, vol. 85, 1976, p. 113, Section 85:41531x.
Herrmann et al., "Method for Alkylating Lactones", J.C.S. Chem. Comm., 1973, pp 711–712.
Koch et al., "Enantioselective Preparation of . . . ", J. Org. Chem., 1993, 58, pp 2725–2737.
K. Mori, "Synthesis of Optically Active Forms of Sulcatol", Tetrahedron, vol. 31, pp 3011–3012.
Kunesch et al., "Structure and Synthesis of the Wing Gland Pheromone of the Male African Sugar–Cane Borere", Tetrahedron Letters, vol. 22, No. 52, pp 5271–5274, 1981.

M. Larcheveque et al., "Absolute Configuration of Eldanolide . . . ," Tetrahedron Letters, vol. 23, No. 48, pp 5051–5054, 1982.
R. E. Doolittle et al., "(S)–Tetrahydro–5–oxo–2–furancarboxylic Acid: A Chiral Derivatizing Reagent for Asymmetric Alcohols", J. Org. Chem., 1984, 49, 5041–5050.
A. Pfenninger, "Asymmetric Epoxidation of Allylic Alcohols: The Sharpless Epoxidation" Reviews, , Chemische Fabrik Uetikon, CH–8707 Uetikon, Switzerland.
Yamanoi et al., "Preparation of Enantiopure 2,2,5,5–Tetramethyl–3,4–hexanediol and Its Use in Catalytic Enantioselective Oxidation of Sulfides to Sulfoxides", J. Org. Chem. 1997, pp 8560–8564.
Louwrier et al., "Studies towards the Synthesis of (+)–Ptilomycalin A; Stereoselective N–Acyliminium Ion Coupling Reactions to Enantiopure C–2 Substituted Lactams", Tetrahedron, vol. 52, No. 7, pp 2603–2628.
Chamberlin et al., "Stereoselective Iodolactionizaiton of Acyclic Unsaturated 3–Hydroxyacids", Tetrahedron Letters, 1981, 22, pp 4611–4614.
Chen et al., "Use of D–Ribonolactone in Organic Synthesis. 2. Scopy and Utility", J. Org. chem., 1984, 49, pp2168–2174.
6–General biochem., vol. 87, 1977, p. 227, Section 87:195626k.
Chemical Abstracts, vol. 96, 1982, p. 236, Section 96:30421n and 96:30422p.
Moret and Schlosser, "A Diastereoselective Synthesis . . . ", Tetrahedron Letters, vol. 25, No. 40, 1984, pp. 4491–4494.
Ortuno, Merce and Font, "Reactions of Some D–Ribonolactone Derivatives . . . ", Tetrahedron, vol. 43, No. 19, pp. 4497–4506.
Cardellach et al., "Studies on Structurally Simple . . . ", Tetrahedron, vol. 38, No. 15, pp. 2377–2394.
Ravid et al., "Synthesis of the Enantiomers . . . ", Tetrahedron , vol. 34, pp. 1449–1452.
Drioli et al., "Synthesis of (+)—and (−)– Phaseolinic . . . ", J. Org. Chem. , 1998, 63, pp. 2385–2388.

* cited by examiner

Primary Examiner—Amelia Owens
(74) Attorney, Agent, or Firm—Sidley Austin Brown & Wood LLP

(57) ABSTRACT

The present invention relates to a novel chiral derivative of Garcinia acid bearing lactone ring moiety of formula I,

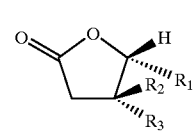

Formula I wherein:
$R_1 = R_3$ = alkali salt of carboxyl acid, or acid chloride or lower esters or part of N-substituted cyclic imides.
$R_2$ = hydroxyl or protected hydroxyl group and a process for preparing the same.

21 Claims, No Drawings

CHIRAL DERIVATIVES OF GARCINIA ACID BEARING LACTONE RING MOIETY AND PROCESS FOR PREPARING THE SAME

FIELD OF INVENTION

This invention relates to novel chiral derivatives bearing lactone moiety of Garcinia acid and a process for preparing the same.

BACKGROUND OF THE INVENTION

Garcinia acid [(−)-Hydroxycitric acid lactone or (2S,3S)-Tetrahydro-3-hydroxy-5-oxo-2,3-furandicarboxylic acid] is isolated from the fruits of *Garcinia cambogia, Garcinia indica* and *Garcinia atroviridis*. Garcinia acid for formula Ia is widely used as an important ingredient in many pharmaceutical formulations[1-10].

The non-availability of Ia in the market, in the pure form, has resulted in the limited use of these compounds in the area of organic synthesis and pharmaceutical front. This is due to the lack of any commercially viable large-scale manufacturing process. In U.S. patent application Ser. No.09/365,301,1999 an economic, commercially viable, cost effective process for the large-scale isolation of Ia has been described[11].

Also during the past two decades there has been a great deal of interest to find cheap and potential chiral molecules from chiral pool to accomplish synthetic pathways with a high degree of asymmetric induction[12-25].

Added to this, substituted γ-butyrolactones are known to be potent antagonists or agonists depending upon the substitution pattern of the γ-aminobutyric acid receptor, the major inhibitory neurotransmitter in the mammalian central nervous system[26].

The known methods for obtaining diversity functionalised chiral γ-lactones are either by the cyclisation of acyclic starting materials such as the sterioselective iodolactonisation of unsaturated 3-hydroxy acids[27] or from sugars such as D-ribofiranose or D-glucosamine or carbohydrates such as D-ribose, D-glucose etc[28]. These chemical: modifications involving carbohydrates require tedious protocols.

SUMMARY OF THE INVENTION

The object of this invention therefore is to prepare novel chiral derivatives of Garcinia acid and the process of preparing the same.

To achieve the objective this invention provides novel chiral derivatives of

Garcinia acid bearing lactone ring moiety of formula I-

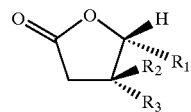

Formula I wherein:

$R_1 = R_3$ = alkali salt of carboxyl acid, or acid chloride or part of N-substituted cyclic imides.

$R_2$ = hydroxyl or protected hydroxyl group.

In the above formula I

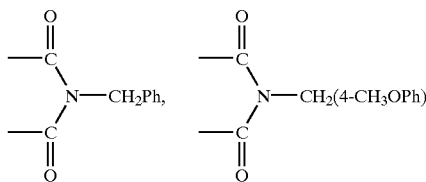

$R_2$ is —OH or protected hydroxyl group. To form various chiral derivatives of Garcinia acid bearing lactone ring moiety.

Chiral Derivatives of Garcinia Acid Bearing Lactone Ring Moiety

| | | |
|---|---|---|
| Ib- | $R_1 = R_3$ = —COONa, | $R_2$ = —OH |
| Ic- | $R_1 = R_3$ = —COCl, | $R_2$ = —OH |
| Id- | $R_1 = R_3$ = —COOCH$_3$, | $R_2$ = —OCH$_2$SCH$_3$ |

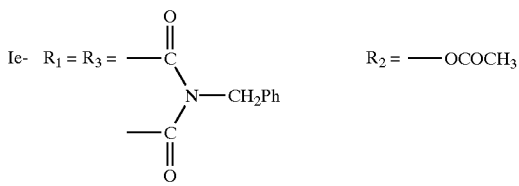

| | | |
|---|---|---|
| If- | $R_1 = R_3$ = —COOCH$_3$, | $R_2$ = —OH |

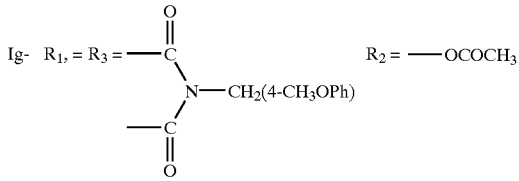

Summary of the chiral derivatives of Garcinia acid bearing lactone ring moiety is given below in scheme I:

| | | |
|---|---|---|
| Ia : | $R_1 = R_3$ = —COOH; | $R_2$ = —OH |
| Ib : | $R_1 = R_3$ = —COONa; | $R_2$ = —OH |
| Ic : | $R_1 = R_3$ = —COCl; | $R_2$ = —OH |
| Id : | $R_1 = R_3$ = —COOCH$_3$; | $R_2$ = —OCH$_2$SCH$_3$ |

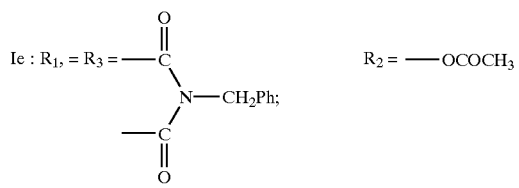

| | | |
|---|---|---|
| If : | $R_1 = R_3$ = —COOCH$_3$; | $R_2$ = —OH |

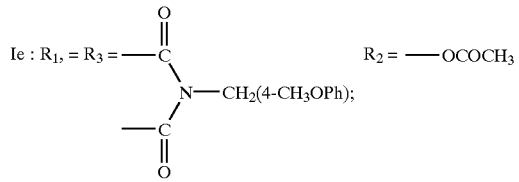

The present invention further provides a process of preparation of Formula Ib comprising:

treating an aqueous solution of Ia with an aqueous solution of alkali till the pH of the solution is neutral, evaporating the solution to dryness, washing the residue with water miscible organic solvent, drying the product Ib in vaccum.

The said alkali is sodium bicarbonate.

The invention further includes a process for the preparation of novel chiral derivative of formula Ic, comprising:

adding an organic halide to a suspension of Ib in organic solvent, stirring the mixture for 1–4 hours, filtering the said mixture, evaporating the said solution to get Ic as a hygroscopic solid.

The said organic solvent is ether.

The said organic halide is thionyl chloride.

The invention further includes a process for the preparation of novel chiral derivative of formula Id comprising:

adding DMSO, an organic acid and an anhydride to If, allowing the mixture to stand for 3–4days, adding the reaction mixture to cold saturated aqueous solution of alkali, stirring the mixture for 1–4 hours, extracting the resultant solution with an organic solvent, washing the extract with aqueous alkali, drying the organic layer, evaporating to get crude Id, purifying the crude Id by chromatography to get pure Id as an yellow oil.

The said organic acid is acetic acid.

The said anhydride is acetic anhydride.

The said alkali is sodium bicarbonate.

The invention further includes a process of preparation of novel chiral derivative of formula Ig comprising:

refluxing the suspension of Ia in an organic halide for 3 hours, concentrating the said mixture under vacuum, dissolving the solid obtained in an organic solvent, adding an appropriate amine to the dissolved solution, stirring the mixture at room temperature for 4–18 hours, concentrating the solution under vacuum, adding the organic halide to the semi-solid obtained, refluxing for 18 hours, extracting with suitable organic solvent, subjecting the said extract to chromatography furnishing Ig as white crystals.

The said organic halide is acetyl chloride.

The said appropriate amine is 4-methoxy benzyl amine.

The said organic solvent is chloroform.

The process will now be described with reference to the following examples.

EXAMPLE 1

Garcinia Acid (Ia)

Dried rinds of the fruits of Garcinia cambogia (2.0 Kg) were cut into small pieces and soaked in hot water. The extract was collected after 20 hours and the process was repeated (4–5 times). The combined extract was concentrated to get a thick mass to which methanol was added. The precipitated pectin was filtered off and the filtrate was further concentrated to a syrup. The syrup was made alkaline by adding sufficient quantity of aqueous sodium hydroxide solution followed by the addition of methanol fill two layers separated. The separated sodium salt of Ia (lower layer) was washed several times with aqueous methanol. The pure sodium salt was dissolved in sufficient quantity of 2N hydrochloric, acid. To the concentrated solution acetone was added to remove insoluble impurities. The filtrate on concentration yielded crude crystals of Garcinia acid. Upon recrystallisation from acetone-chloroform mixture yielded crystals of Ia in high purity.

Melting point :178° C.

Yield: 135.0 g

EXAMPLE 2

Disodium(2S,3S)-tetrahydro-3-hydroxy-5oxo-2,3-furandicarboxylate (Ib)

To an aqueous solution of Ia (2.0 g, 10.5 mmol, in 10 ml water) saturated sodium bicarbonate solution was added till the pH of the solution is neutral. The residue obtained after evaporation was washed with dry acetone (5×20 ml). The product Ib was finally dried under vacuum.

Yield: 2.0 g (82%).

EXAMPLE 3

(2S,3S)-tetrahydro-3-hydroxy-5oxo2,3-furandicarbonylchloride (Ic)

To a suspension of Ib (1.0 g, 4.4 mmol) in ether (10 ml), thionyl chloride ( 1.0 ml, 14 mmol) was added. The mixture was stirred for two hours. Filtration followed by evaporation of the reaction mixture yielded Ic. Yield: 0.75 g (65%).

EXAMPLE 4

Dimethyl(2S,3S)-tetrahydro3-oxo-[(methylthio)methoxy]-5ox-2,3-furandicarboxylate (Id)

To a solution of If (2 g, 9.2 mmol) in DMSO (28 ml), acetic acid (3.5 ml) in acetic anhydride (20 ml) was added. The mixture was allowed to stand for three days. The reaction mixture was added to saturated aqueous solution of sodium bicarbonate (400 ml) and stirred for one hour. It was extracted with chloroform (3×125 ml) and the combined chloroform extracts was washed: with saturated sodium bicarbonate solution (100 ml) followed by water (2×50 ml). The chloroform extract was dried (sodium sulphate) and evaporated to get crude Id (1.5 g). Id was further purified by column chromatography (silicagel 60–120 mesh, eluent: hexane-chloroform, 10–50%)

Yield: 0.75 g (29%)

EXAMPLE 5

(3aS,6aS)-3a-(acetyloxy)dihydro5(phenylmethyl)6Hfuro[2,3-c]pyrrole-2,4,6 (3H,4H)-trione) (Ie)

A suspension of Ia (1g, 5 mmol) in acetyl chloride (4 ml) was refluxed for 3 hours followed by concentration under vacuum. The solid obtained was dissolved in THF (5 ml) and benzyl amine (0.535 ml, 5 mmol) was added. The mixture was stirred at room temperature for 4 hours and concentrated in vacuum. To the semi-solid obtained acetyl chloride (5 ml) was added and the mixture was refluxed for 18 hours. Extraction using ethyl acetate followed by recrystallisation from hexane—ethyl acetate furnished Ie as white crystals.

Melting point: 156–157° C.

Yield: 0.75 g. (52%)

Uses

Pharmaceutical applications

Chiral derivatives, Ia–Ig, are used as chiral synthons.

We claim:

1. A novel chiral derivative of Garcinia acid bearing lactone ring moiety of formula I,

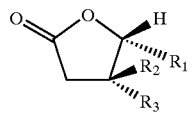

Formula I wherein:

R$_1$=R$_3$=alkali salt of carboxyl acid, or acid chloride or part of N-substituted cyclic imides.

R$_2$=hydroxyl or protected hydroxyl group.

2. A derivative as claimed in claim 1 wherein

R$_1$ & R$_3$ is selected from —COONa, —COCl,

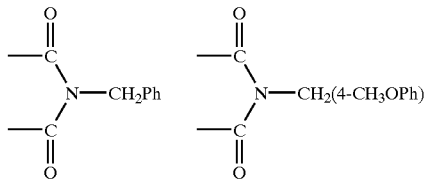

R$_2$ is —OH or protected hydroxyl group.

3. A derivative as claimed in claim 1 wherein R$_1$=R$_3$=—COONa, R$_2$=—OH and said derivative is Disodium(2S,3S)-tetrahydro-3-hydroxy-5-oxo-2,3-furandicarbonylchloride

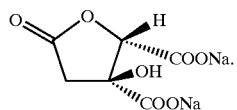

4. A derivative as claimed in claim 1 wherein R$_1$=R$_3$=—COCl,

R$_2$=—OH and said derivative is (2S,3S)-tetrahydro-3-hydroxy-5-oxo-2,3-furandicarbonylchloride

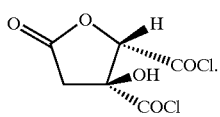

5. Dimethyl(2S,3S)-tetrahydro-3-oxo-[(methylthio)methoxy]-5-oxo-2,3-furandicarboxylate

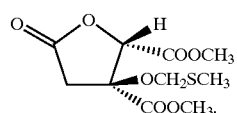

6. A derivative as claimed in claim 1 wherein

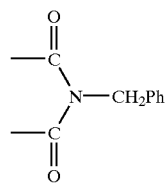

R$_2$=—OCOCH$_3$ and said derivative is (1S,5S)-7-5-acetoxy-2-oxo-7-azabicyclo[3,3,0]octane-3,6,8-trione

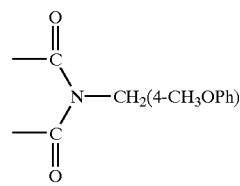

7. A derivative as claimed in claim 1 wherein

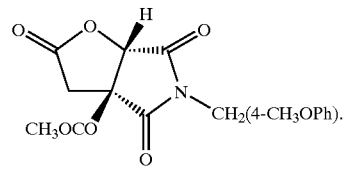

R$_2$=—OCOCH$_3$

8. A process for the preparation of novel chiral derivative of formula Ib, as claimed in claim 3, comprising:
treating an aqueous solution of Ia with an aqueous solution of alkali till the pH of the solution is neutral,
evaporating the solution to dryness,
washing the residue with water miscible organic solvent,
drying the product Ib in vaccum.

9. A process for the preparation of novel chiral derivative of formula Ic as claimed in claim 4, comprising:
adding an organic halide to a suspension of Ib in organic solvent,
stirring the mixture for 1–4 hours,
filtering the said mixture,
evaporating the said solution to get Ic as a hygroscopic solid.

10. A process for the preparation of novel chiral derivative for formula Id as claimed in claim 5 comprising:
adding DMSO, an organic acid and an anhydride to If,
allowing the mixture to stand for 3–4 days,
adding the reaction mixture to cold saturated aqueous solution of alkali,
stirring the mixture for 1–4 hours,
extracting the resultant solution with an organic solvent, washing the extract with aqueous alkali, drying the organic layer, evaporating to get crude Id, purifying the crude Id by chromatography to get pure Id as an yellow oil.

11. A process of preparation of novel chiral derivative of formula Ie as claimed in claim 6 comprising:

refluxing the suspension of Ia in an organic halide for 3 hours, concentrating the said mixture under vacuum, dissolving the solid obtained in an organic solvent, adding an appropriate amine to the dissolved solution, stirring the mixture at room temperature for 4–18 hours, concentrating the solution under vacuum, adding the organic halide to the semi-solid obtained, refluxing for 18 hours, extracting with suitable organic solvent, subjecting the said extract to chromatography furnishing Ie as white crystals.

12. A process as claimed in claim 8 wherein, the said alkali is sodium bicarbonate.

13. A process as claimed in claim 10 wherein, the said alkali is sodium bicarbonate.

14. A process, as claimed in claim 9 wherein, the said organic solvent is ether.

15. A process as claimed in claim 9 wherein, the said organic halide is thionyl chloride.

16. A process, as claimed in claim 10 wherein, the said organic acid is acetic acid.

17. A process, as claimed in claim 10 wherein, the said anhydride is acetic anhydride.

18. A process, as claimed in claim 10 wherein, the said organic solvent used for extraction is chloroform.

19. A process, as claimed in claim 11 wherein, the said organic solvent used for extraction is chloroform.

20. A process as claimed in claim 11 wherein, the said appropriate amine is benzyl amine.

21. A process as claimed 11 wherein, the said appropriate amine is 4-methoxy benzyl amine.

* * * * *